(12) United States Patent
Jyothi Prasad et al.

(10) Patent No.: US 8,349,855 B2
(45) Date of Patent: Jan. 8, 2013

(54) POLYMORPHS OF ERLOTINIB HYDROCHLORIDE AND METHOD OF PREPARATION

(75) Inventors: Ramanadham Jyothi Prasad, Hyderabad (IN); Bhujanga rao Adibhatla Kali Satya, Hyderabad (IN); Nannapaneni Venkaiah Chowdary, Hyderabad (IN)

(73) Assignee: Natco Pharma Limited, Hyderabad, Andhra Pradesh (IN)

( * ) Notice: Subject to any disclaimer, the term of this patent is extended or adjusted under 35 U.S.C. 154(b) by 290 days.

(21) Appl. No.: 12/672,191

(22) PCT Filed: Sep. 11, 2007

(86) PCT No.: PCT/IN2007/000407
§ 371 (c)(1),
(2), (4) Date: Jun. 21, 2010

(87) PCT Pub. No.: WO2008/102369
PCT Pub. Date: Aug. 28, 2008

(65) Prior Publication Data
US 2010/0261738 A1 Oct. 14, 2010

(30) Foreign Application Priority Data
Feb. 21, 2007 (IN) .............................. 349/CHE/2007

(51) Int. Cl.
*A61K 31/517* (2006.01)
(52) U.S. Cl. ..................................... 514/266.4; 544/293
(58) Field of Classification Search .................... 544/293
See application file for complete search history.

(56) References Cited

U.S. PATENT DOCUMENTS
5,747,498 A 5/1998 Schnur et al.
6,476,040 B1 11/2002 Norris et al.
6,900,221 B1 5/2005 Norris et al.

FOREIGN PATENT DOCUMENTS
| WO | WO 96/30347 | 10/1996 |
| WO | WO 01/34574 | 5/2001 |
| WO | WO 2004/072049 | 8/2004 |
| WO | WO 2007/060691 | 5/2007 |
| WO | WO 2007/138613 | 12/2007 |

OTHER PUBLICATIONS
International Search Report from PCT/IN2007/000407 dated May 14, 2008 (Form PCT/ISA/210).

*Primary Examiner* — Brian McDowell
(74) *Attorney, Agent, or Firm* — Merchant & Gould P.C.

(57) ABSTRACT

The present invention relates to three novel crystalline forms of Erlotinib hydrochloride and method of preparation thereof. Erlotinib hydrochloride is N-(3-ethynylphenyl)-6,7-bis(2-methoxy ethoxy)-4-quinazolinamine hydrochloride of formula-(I).

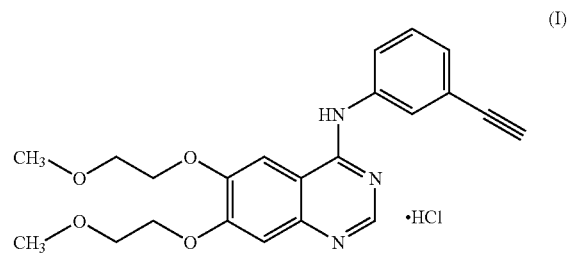

Figure 1:
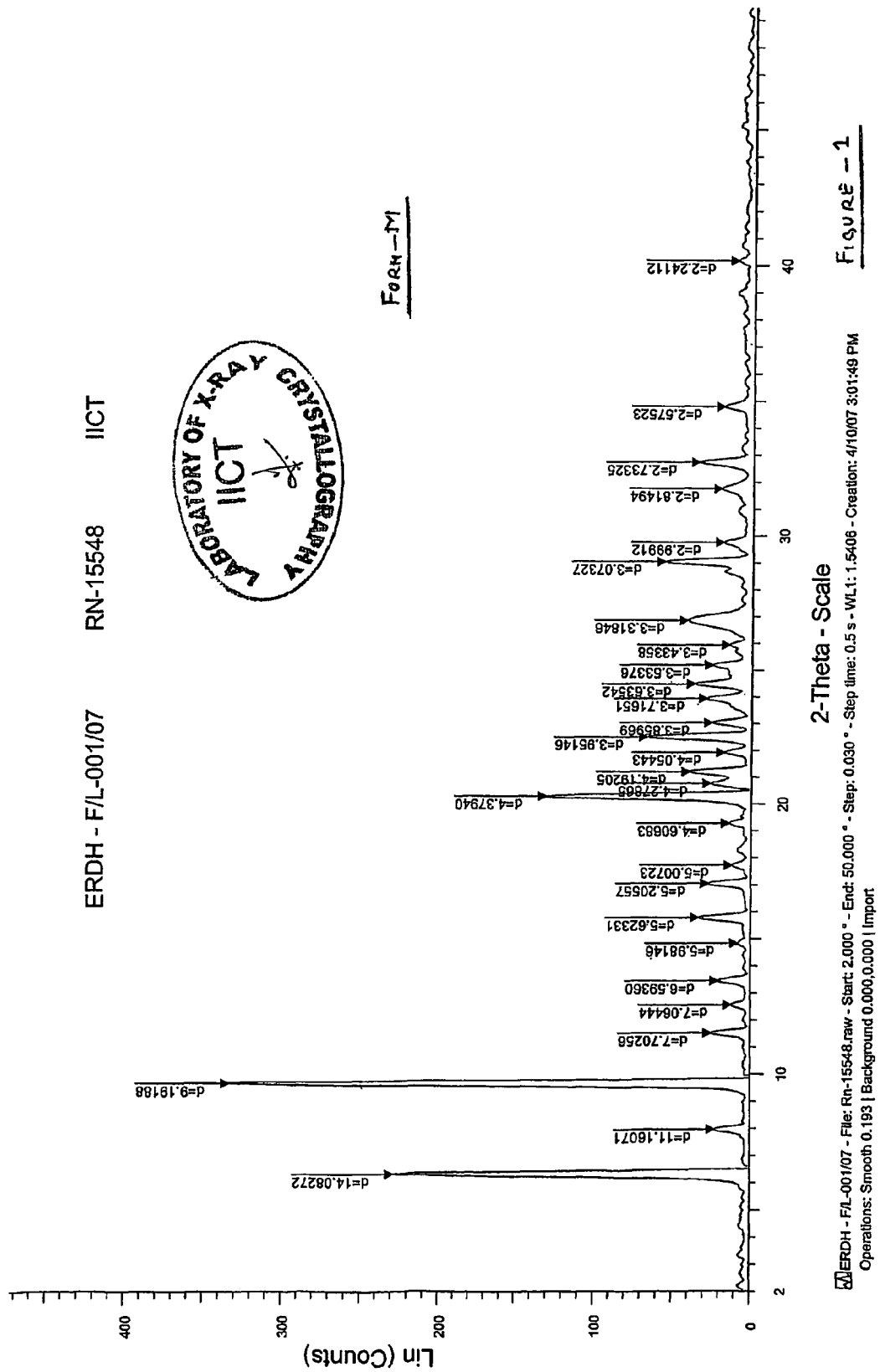

The present invention provides stable novel crystalline forms of Erlotinib hydrochloride designated as Form-M, Form-N and Form-P, and processes for the preparation of the same. Erlotinib hydrochloride can be used as medicament for the treatment of hyperproliferative disorders, such as cancers, in humans.

4 Claims, 3 Drawing Sheets

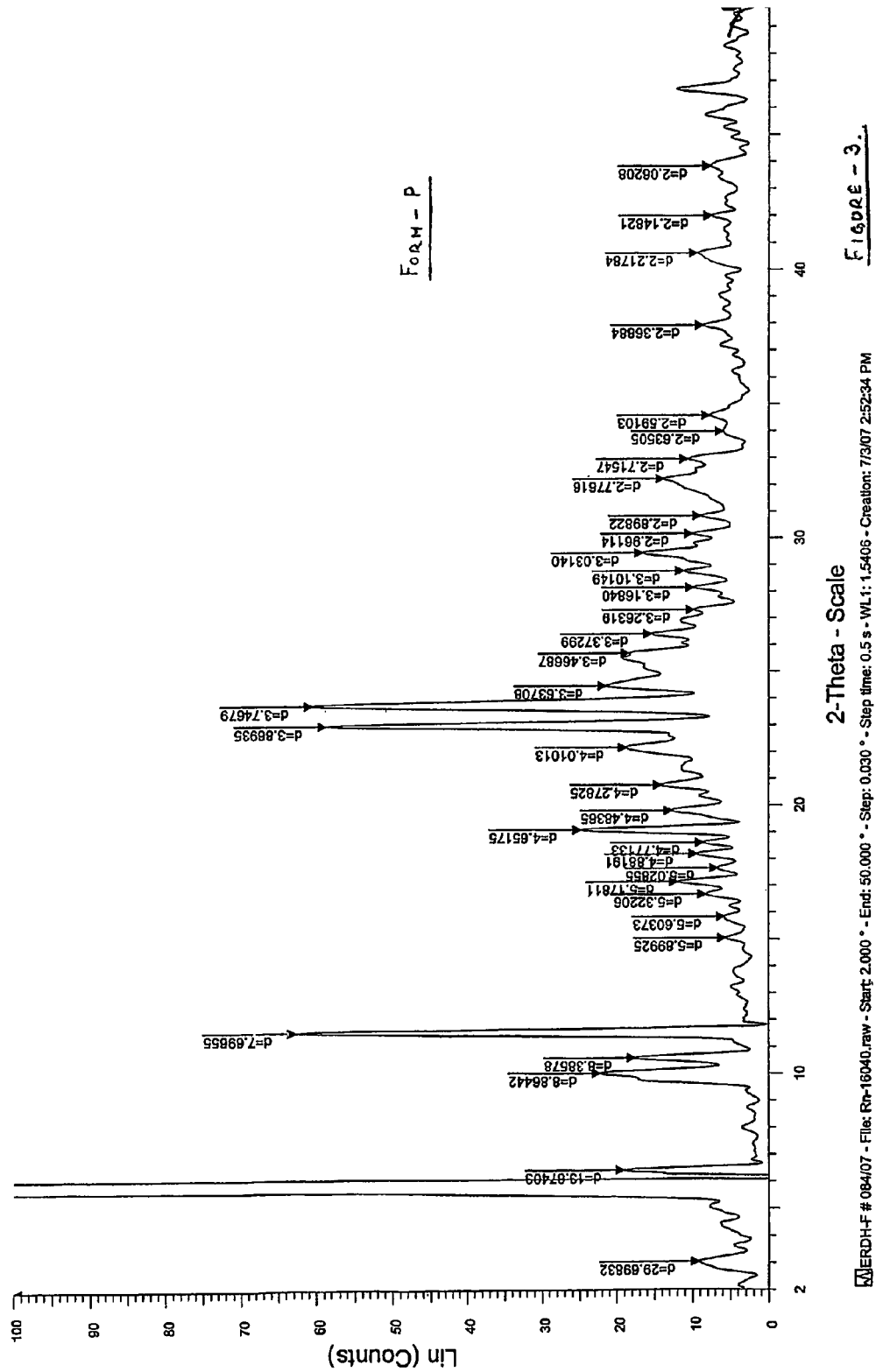

POLYMORPHS OF ERLOTINIB HYDROCHLORIDE AND METHOD OF PREPARATION

This application is a National Stage Application of PCT/IN2007/000407, filed 11 Sep. 2007, which claims benefit of Ser. No. 349/CHE/2007, filed 21 Feb. 2007 in India and which applications are incorporated herein by reference. To the extent appropriate, a claim of priority is made to each of the above disclosed applications.

The present invention relates to three novel polymorphic forms Form-M, Form-N and Form-P of Erlotinib Hydrochloride of formula-(I). Erlotinib is N-(3-ethynylphenyl)-6,7-bis(2-methoxy ethoxy)-4-quinazolinamine and is an inhibitor of the erbB family of oncogenic and protooncogenic protein tyrosine kinases, such as epidermal growth factor receptor (EGFR). It is therefore useful in the treatment of prolifirative disorders, such as

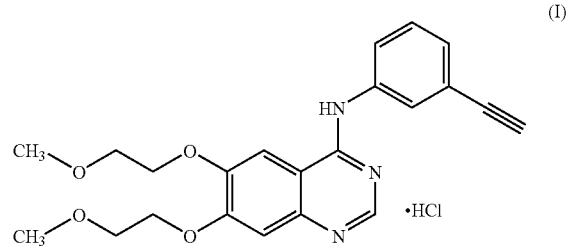 [SMILES: C#Cc1cccc(Nc2ncnc3cc(OCCOC)c(OCCOC)cc23)c1 ; Cl]

(I)

cancers, in humans and often used as its hydrochloride salt (I).

BACKGROUND OF THE PRESENT INVENTION

Erlotinib having the chemical name N-(3-ethynylphenyl)-6,7-bis(2-methoxyethoxy)-4-quinazolinamine, is reported in PCT Publication No. WO. 96/30347 and its equivalent U.S. Pat. No. 5,747,498 (1998). Although, the preparation of its hydrochloride salt is mentioned in this patent, its Polymorphic forms and their properties are not discussed. None of its solid state properties excepting melting point are disclosed in this patent.

Subsequently, PCT Publication No. WO. 01/34574 and its equivalent U.S. Pat. No. 6,900,221 (2005) described polymorphic Forms-A and B of Erlotinib HCl, and mentioned that the polymorphic form 'B' is thermodynamically more stable. This patent, also identified that the product of U.S. Pat. No. 5,747,498 was a mixture of polymorphic Forms A and B. A method of preparing pure polymorphic Form-B of Erlotinib. HCl (I) free of the polymorphic Form-A is also claimed in U.S. Pat. No. 6,900,221. The powder XRD data of both the crystal Forms A and B are disclosed in this patent.

The patent WO 2004/072049 corresponding to the International Application No PCT/EP 2004/001244 discloses a novel polymorph E along with its DSC and XRD characteristics and claims improved stability over the polymorph A. However, this polymorphic form E is prepared in (α,α,α)-trifluorotoluene which is highly flammable and dangerous for the environment. It is also an expensive solvent and not convenient to handle on an industrial scale.

SUMMARY OF THE INVENTION

Our continued efforts on the investigation of stable polymorphic forms of Erlotinib HCl resulted in the invention of three novel stable crystal forms designated as Form-M, Form-N and Form-P. The three new polymorphic forms Form-M, Form-N and Form-P are surprisingly and unexpectedly very stable in the solid state at room temperature (30°-35° C.) and also at higher temperatures of the order of 60°-120° C. The novel polymorphic forms mentioned can be easily prepared by employing inexpensive and commercially available solvents like isopropanol, methanol and methylene chloride which are suitable for large scale manufacture. Thus the novel Form-M of Erlotinib. HCl is prepared by treating Erlotinib base in methanol with a solution of HCl in dry methanol or isopropanol. Similarly the novel form-N is prepared by treating erlotinib base in isopropanol with isopropanolic HCl and Form-P is prepared by treating Erlotinib base in methylene chloride with isopropanolic HCl. The three novel forms, Form-M, Form-N and Form-P of Erlotinib HCl are characterized by Powder XRD pattern and are very stable in solid state.

Therefore the main objective of the present invention is to provide stable novel crystalline forms of Erlotinib HCl designated as Form-M, Form-N and Form-P.

Another objective of the present invention is to provide processes for the preparation of stable novel crystalline forms of Erlotinib HCl designated as Form-M, Form-N and Form-P.

Figure 2:
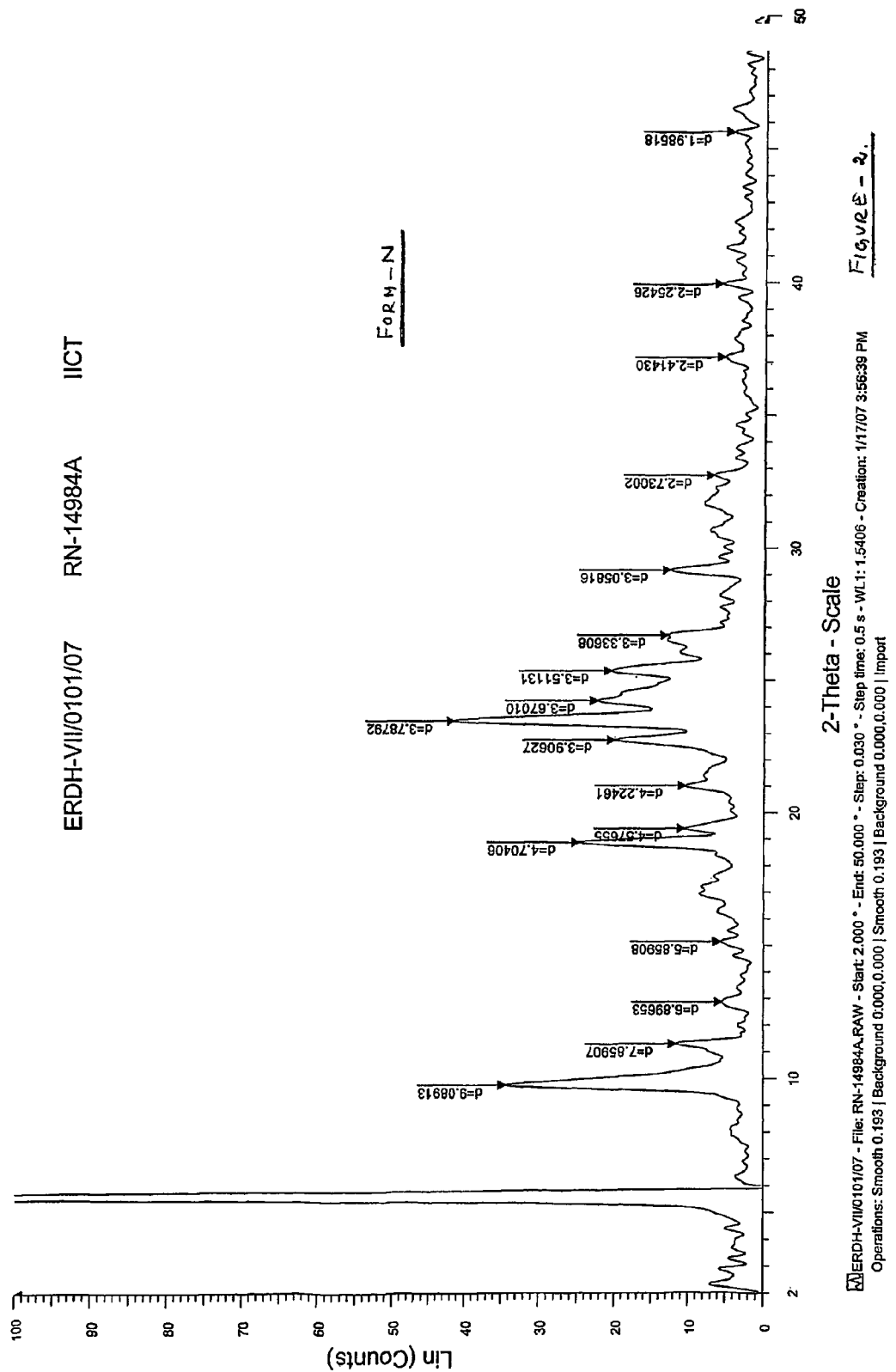

Accordingly the present invention provides novel stable crystalline forms of Erlotinib HCl designated as Form-M, Form-N and Form-P, having the characteristics as given below.:

X-Ray Powder Diffraction Pattern:
(i) Form-M: having typical characteristic peaks at about 6.2, 7.9, 9.6, 11.4, 12.5, 13.4, 14.7, 15.7, 17.0, 17.6, 19.2, 20.2, 20.7, 21.1, 21.9, 22.4, 23.0, 23.9, 24.4, 25.1, 25.9, 26.8, 29.0, 29.7, 31.7, 32.7, 34.8, 40.2 on the 2θ scale as shown in FIG. 1.
(ii) Form-N: having typical characteristic peaks at about 5.56, 9.72, 11.25, 12.82, 18.84, 19.38, 21.01, 22.74, 23.46, 24.23, 25.34, 26.70, 29.17, 32.77, 37.21, 39.96, 45.66 on the 2θ scale as shown in FIG. 2.
(iii) Form-P: having typical characteristic peaks at about 2.97, 5.80, 6.36, 9.97, 10.54, 11.48, 15.00, 15.80, 16.64, 17.11, 17.62, 18.15, 18.58, 19.06, 19.78, 20.74, 22.14, 22.96, 23.72, 24.45, 25.67, 26.40, 27.30, 28.14, 28.76, 29.44, 30.15, 30.82, 32.21, 32.95, 33.99, 34.59, 40.49, 40.64, 42.02, 43.87 on the 2θ scale as shown in FIG. 3.

According to another feature of the present invention, there are provided processes for the preparation of the novel crystalline forms Form-M, Form-N and Form-P of Erlotinib Hydrochloride of formula-(I), having the above mentioned characteristics which

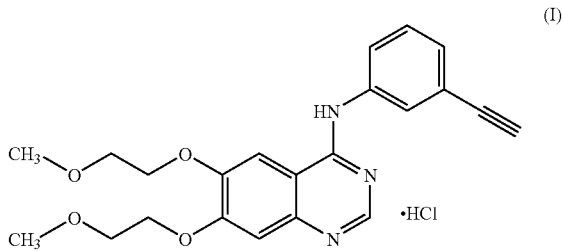 [SMILES: C#Cc1cccc(Nc2ncnc3cc(OCCOC)c(OCCOC)cc23)c1 ; Cl]

(I)

comprise:
(i) Dissolving Erlotinib base (prepared according to the process given in International Publication No.: WO. 2007/060691) in dry methanol and adding a solution of dry HCl gas in methanol or isopropanol. The crystals of Erlotinib HCl thus obtained are dried and designated as Form-M.

(ii) Dissolving Erlotinib base (prepared according to the process given in International Publication No.: WO. 2007/060691) in dry isopropanol and adding a solution of dry HCl gas in isopropanol. The crystals of Erlotinib HCl are filtered and dried and designated as Form-N.

(iii) Dissolving Erlotinib base (prepared according to the process given in International Publication No.: WO. 2007/060691) in dry methylene chloride and adding a solution of dry HCl gas in isopropanol. The crystals of Erlotinib HCl are filtered and dried and designated as Form-P.

The following examples are given for the purpose of illustrating the process of the present invention and therefore should not be considered to limit the scope or spirit of the invention.

EXAMPLE-1

Preparation of Erlotinib HCl Polymorphic Form-M:

Into a 2 Lt. four necked round-bottomed flask provided with a mechanical stirrer, thermometer socket, reflux condenser etc are charged 1340 mL of methanol, followed by Erlotinib base 60 g. (Prepared according to the process given in Example-(1) of PCT international publication No. WO2007/060691). The reaction mass is warmed to around 40° C. so that Erlotinib base completely dissolves. To this reaction mass, carbon treatment is given and the filtrate is transferred to another 2 Lt. four necked flask. To this solution isopropanolic HCl (HCl content as 100% is 6.12 g) is added in one lot and the reaction mass is stirred at 30-35° C. for about 90 minutes and filtered. The product is washed with fresh methanol and dried the wet cake to get 55.2 g of Erlotinib hydrochloride as a white crystalline powder.

XRPD: Form-M (FIG. 1)

EXAMPLE-2

Preparation of Erlotinib HCl Polymorphic Form-N:

Into a 1 Lt. four necked round-bottomed flask provided with a mechanical stirrer, thermometer socket, reflux condenser etc, are charged 325 mL of isopropyl alcohol, followed by 25.0 g of Erlotinib base (Prepared according to the process given in Example-(1) of PCT international publication No. WO2007/060691) at 70-75° C. so that Erlotinib base completely dissolves in the solvent. Then carbon treatment is given and the filtrate is transferred to another 1 Lt. four-necked round bottomed flask provided with all the necessary accessories. To this solution isoproponolic HCl (HCl content as 100% is 2.548 g) is added in one lot at 60-65° C. and maintained at this temperature for about 1 hour. The reaction mass is cooled to room temperature and filtered. The product is washed with fresh isopropyl alcohol and dried to get 25.0 g of Erlotinib hydrochloride as a white crystalline powder.

XRPD: Form-N (FIG. 2)

EXAMPLE-3

Preparation of Erlotinib HCl Polymorphic Form-P:

Into a 3 Lt. four necked round-bottomed flask provided with a mechanical stirrer, thermometer socket, reflux condenser etc, are charged 2400 mL of methylene chloride, followed by 120 g of Erlotinib base (Prepared according to the process given in Example-(1) of PCT international publication No. WO2007/060691) under stirring. The reaction mass is slightly warmed up to 37±1° C., so that the Erlotinib base completely dissolves in the solvent. Then carbon treatment is given and the filtrate is transferred to 5 Lt three necked round bottomed flask, provided with a mechanical stirrer and other accessories. To this filtrate, Isopronolic HCl. (HCl content as 100% is 13.90 g) is added in one lot at 30-35° C. and then the reaction mass is refluxed for about 3 hrs. Afterwards, the reaction mass is cooled to room temperature and filtered. The product is washed with methylene chloride and the wet cake is dried to get 119 g of Erlotinib hydrochloride as a white crystalline powder.

XRPD: Form-P (FIG. 3)

EXAMPLE-4

Preparation of Erlotinib Hydrocloride, Polymorphic Form-P:

(i) Preparation of N-(3-ethynylphenyl)-6,7-bis(2-methoxyethoxy)-4-quinazolinamine (Erlotinib Base)

For the preparation of Erlotinib base, the starting intermediate N-(3-ethynyl phenyl)-6,7-dihydroxy-4-quinazolinamine, is obtained from the process described in steps (i) to (v) of Example-(1) of PCT international publication No. WO 2007/060691.

Into a clean and dry stainless steel reactor, are charged 250 Lts of dimethyl formamide, followed by 30 Kgs of potassium carbonate (anhydrous) and 10 Kgs of N-(3-ethynyl phenyl)-6,7-dihydroxy-4-quinazolinamine under nitrogen atmosphere. To this reaction mixture 14.0 Kgs of 2-Iodo ethyl methyl ether is added and maintained at 45-50° C. for about 12 hrs and the reaction is found to be completed by HPLC-Test. Then the reaction mass is cooled to room temperature and the mass is centrifuged to remove the inorganic salt.

To the collected filtrate, demineralized water is slowly added, under stirring below 35° C., so that the product is crystallized out. Then the product is centrifuged and washed with water and the wet cake is dried to get 9.8 Kgs (69% by theory) of Erlotinib base as a brownish yellow coloured crystalline solid.

Purity: 99.17% (by HPLC)

Melting range: 151-153° C.

(ii) Purification of Erlotinib Base

Erlotinib base of high purity is obtained by adopting the following purification method. Into a clean and dry All Glass Reactor, are charged 90 Lts of methylethyl ketone, followed by 9 Kgs of Erlotinib base obtained by the process described in Step-(i) above. The temperature is raised to 60-65° C. to dissolve the solid completely. Carbon treatment is given and the filtrate is cooled to 10° C. and centrifuged the crystallized product and washed the cake with methyethyl ketone and the wet cake is dried to get 5.9 Kgs of Erlotinib base of high purity, as a pale yellow coloured crystalline solid.

Purity: 99.74% (by HPLC)

Melting range: 154-155° C.

(iii) Preparation of Erlotinib Hydrochloride, Polymorphic Form-P

Into a clean and dry All Glass Reactor, are charged 110 Lts of methylene chloride, followed by 5.5 Kgs of Erlotinib base as obtained from step-(ii) above. The temperature is raised to 37±1° C. so that the solid completely dissolves. To this carbon treatment is given and the filtrate is transferred into another clean and dry All glass reactor. To this reaction mass isoproponic HCl (HCl content as 100% is 0.6371 Kg) is added in one lot at 25-35° C. and then the reaction is maintained at reflux condition for 3 hrs. The reaction mass is cooled to room temperature and centrifused. The product cake is washed with methylene chloride and dried to get 5.5 Kgs of Erlotinib hydrochloride as a white crystalline powder.

Purity: 99.82% (by HPLC)
XRPD: Form-P (identical to FIG. 3)

Advantages of the Present Invention

1) The novel polymorphic forms, Form-M, Form-N and Form-P of Erlotinib hydrochloride are prepared easily and are very stable at room temperature (30-35° C.) and also at elevated temperatures like 60-120° C.
2) The novel polymorphic forms, Form-M, Form-N and Form-P are prepared in inexpensive solvents like isopropanol and methanol and methylene chloride and can be easily scaled-up to manufacturing level.
3) The procedures for preparing the new polymorphic form of Erlotinib hydrochloride (Form-M, Form-N and Form-P) are consistently reproducible.
4) The novel polymorphs M, Form-N and Form-P of Erlotinib hydrochloride are prepared from Erlotinib base purified by a crystallization technique and devoid of any cumbersome chromatographic methods.

We claim:

1. A stable crystalline polymorph of the hydrochloride salt of N-(3-ethynylphenyl)6,7-bis(2-methoxy ethoxy)-4-quinazolinamine designated as Form-P, characterized by an x-ray powder diffraction pattern having characteristic peaks expressed in degrees 2-theta at approximately 2.97, 5.80, 6.36, 9.97, 10.54, 11.48, 15.00, 15.80, 16.64, 17.11, 17.62, 18.15, 18.58, 19.06, 19.78, 20.74, 22.14, 22.96, 23.72, 24.45, 25.67, 26.40, 27.30, 28.14, 28.76, 29.44, 30.15, 30.82, 32.21, 32.95, 33.99, 34.59, 40.49, 40.64, 42.02, 43.87.

2. The crystalline polymorph of claim 1, characterized by an x-ray powder diffraction pattern shown in FIG. 3.

3. A pharmaceutical composition comprising a pharmaceutically acceptable carrier, adjuvant, or mixture thereof and the Form-P polymorph of claim 1.

4. A pharmaceutical composition comprising a pharmaceutically acceptable carrier, adjuvant, or mixture thereof and the Form-P polymorph of claim 2.

* * * * *